United States Patent

Liang

Patent Number: 5,429,585
Date of Patent: Jul. 4, 1995

[54] MULTI-FUNCTION CUSHION

[76] Inventor: Simon Liang, P.O. Box 82-144, Taipei, Taiwan

[21] Appl. No.: 5,355

[22] Filed: Jan. 19, 1993

[51] Int. Cl.⁶ .......................... A61H 1/00; A61N 2/00
[52] U.S. Cl. ...................................... 601/15; 601/57; 601/49; 601/64; 600/9
[58] Field of Search ................. 128/24.1, 24.2, 32–36, 128/41; 600/9

[56] References Cited

U.S. PATENT DOCUMENTS

| | | | |
|---|---|---|---|
| 2,667,866 | 2/1954 | Hart | 128/24.1 |
| 2,792,830 | 5/1957 | Dacey | 128/24.1 |
| 2,943,620 | 7/1960 | Sibert | 128/24.1 |
| 3,885,553 | 5/1975 | Vecchio | 128/33 |
| 4,136,685 | 1/1979 | Ramey | 128/33 |
| 4,143,435 | 3/1979 | Masuda | 600/9 |
| 4,228,793 | 11/1980 | Ramey | 128/33 |
| 4,326,506 | 4/1982 | Kawabata | 128/33 |
| 4,509,219 | 4/1985 | Yagi | 600/9 |
| 4,592,345 | 6/1986 | Wahl | 128/33 |
| 4,607,624 | 8/1986 | Jefferson | 128/24.2 |
| 5,035,017 | 7/1991 | Komuro | 600/9 |
| 5,161,272 | 11/1992 | Yamatguchi et al. | 600/9 X |

Primary Examiner—Robert A. Hafer
Assistant Examiner—Brian E. Hanlon
Attorney, Agent, or Firm—Morton J. Rosenberg; David I. Klein

[57] ABSTRACT

A multi-function cushion is provided having a slip cover, a soft pad enclosed within the slip cover, and having a plurality of magnets on the front side. A control panel with an outer instruction cover coupled to an inner housing chamber is disposed within a recess formed in the soft pad. The control panel includes a vibration switch, a heating switch and a power socket. A heating device is mounted between the front side of the soft pad and the slip cover, and is electrically connected with the heating switch of the control panel. A vibration motor disposed in the rear side of the soft pad is electrically connected with the vibration switch and the power socket of the control panel. A pressure switch is installed in the rear side of the soft pad and electrically connected with the power socket, the vibration switch and the heating device, whereby the cushion not only can support the user's lumbar region, but can also provide heating and massaging effects, and magnetic stimulation of the user.

1 Claim, 10 Drawing Sheets

MULTI-FUNCTION CUSHION

BACKGROUND OF THE INVENTION

Figure 1:
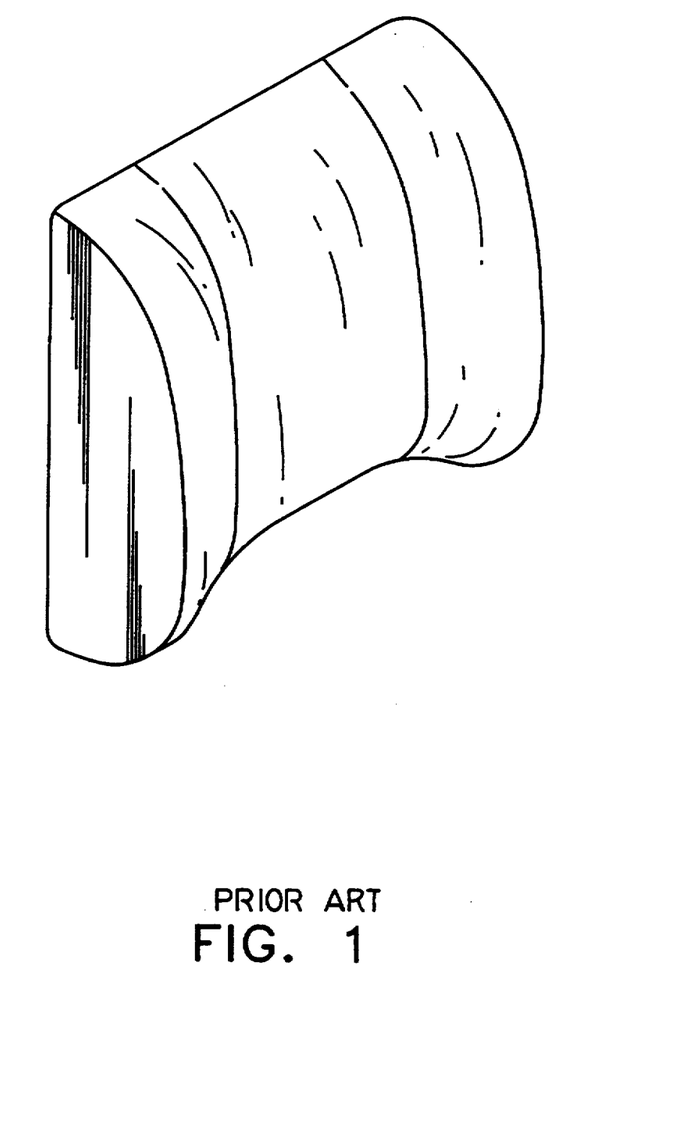
FIG. 1 is a perspective view of a prior art cushion.
Figure 2:
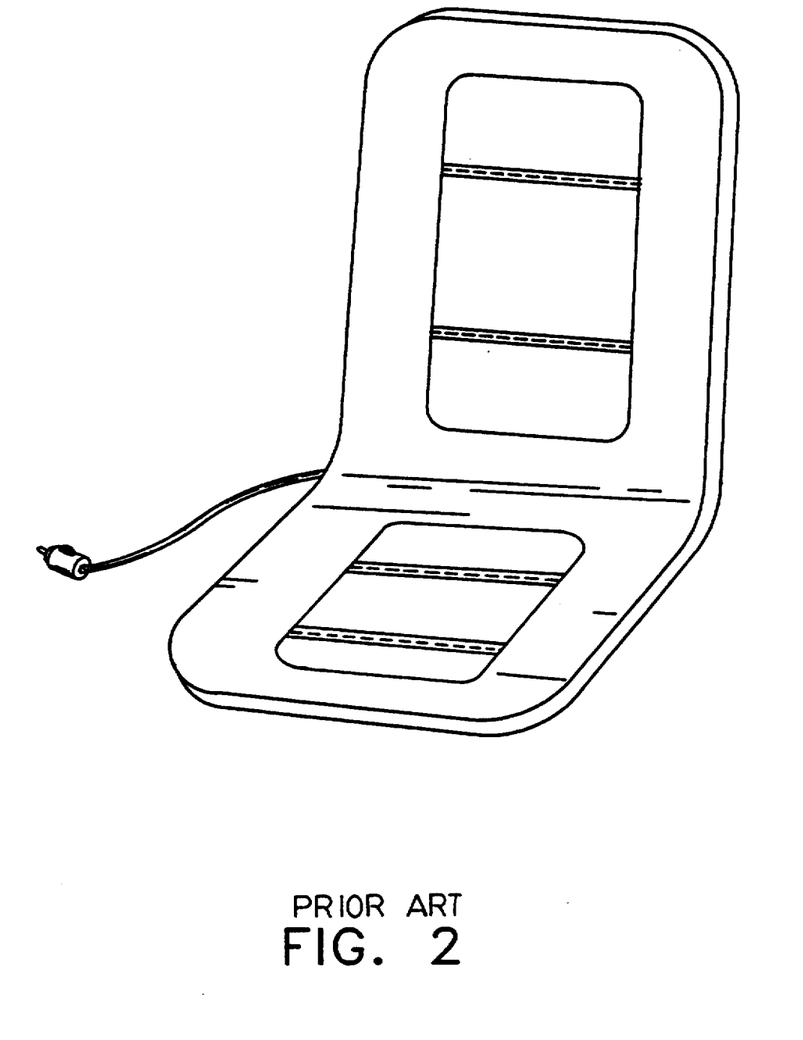
FIG. 2 is a perspective view of a second prior art cushion.
Figure 3:
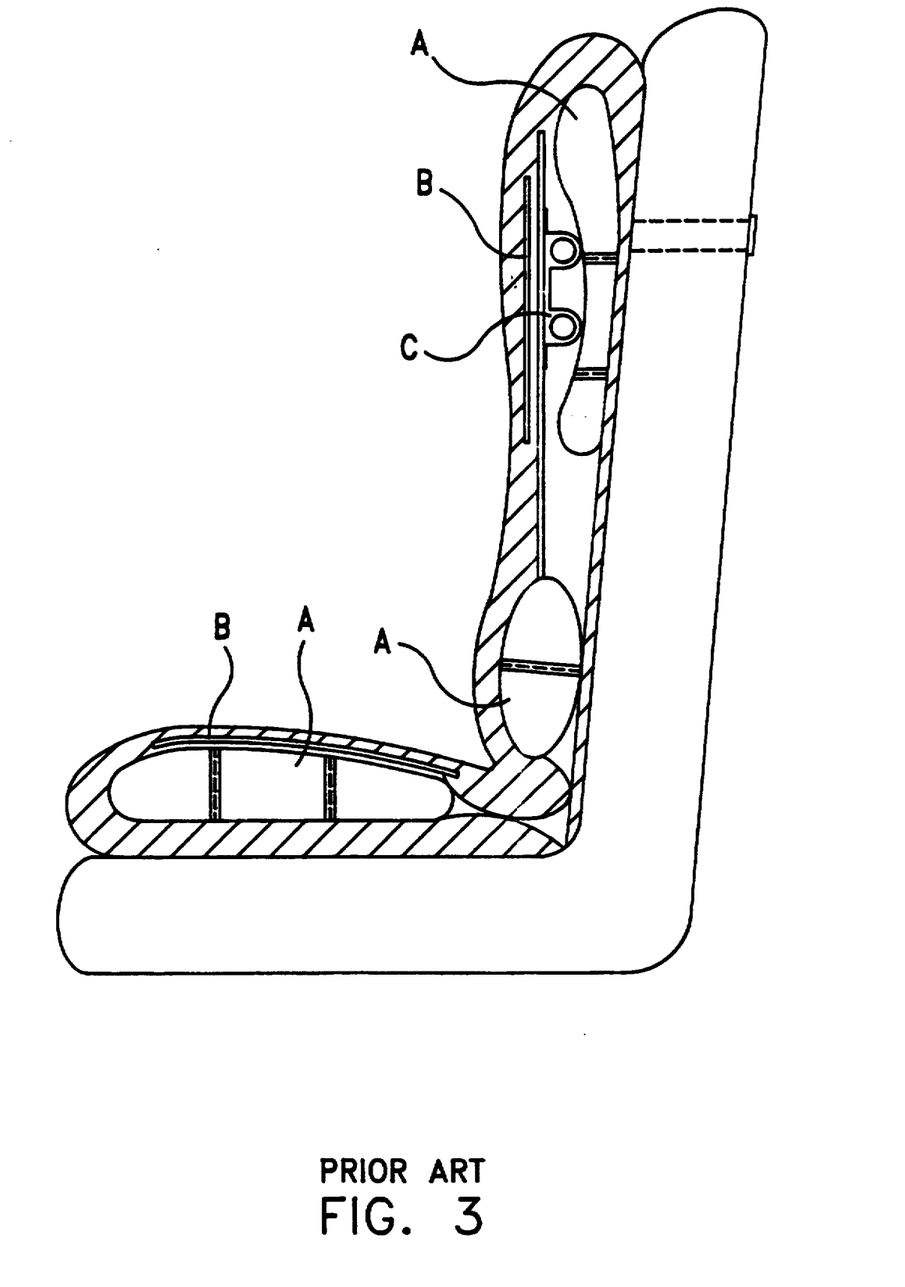
FIG. 3 is a sectional side view of a third prior art cushion.
Figure 4:
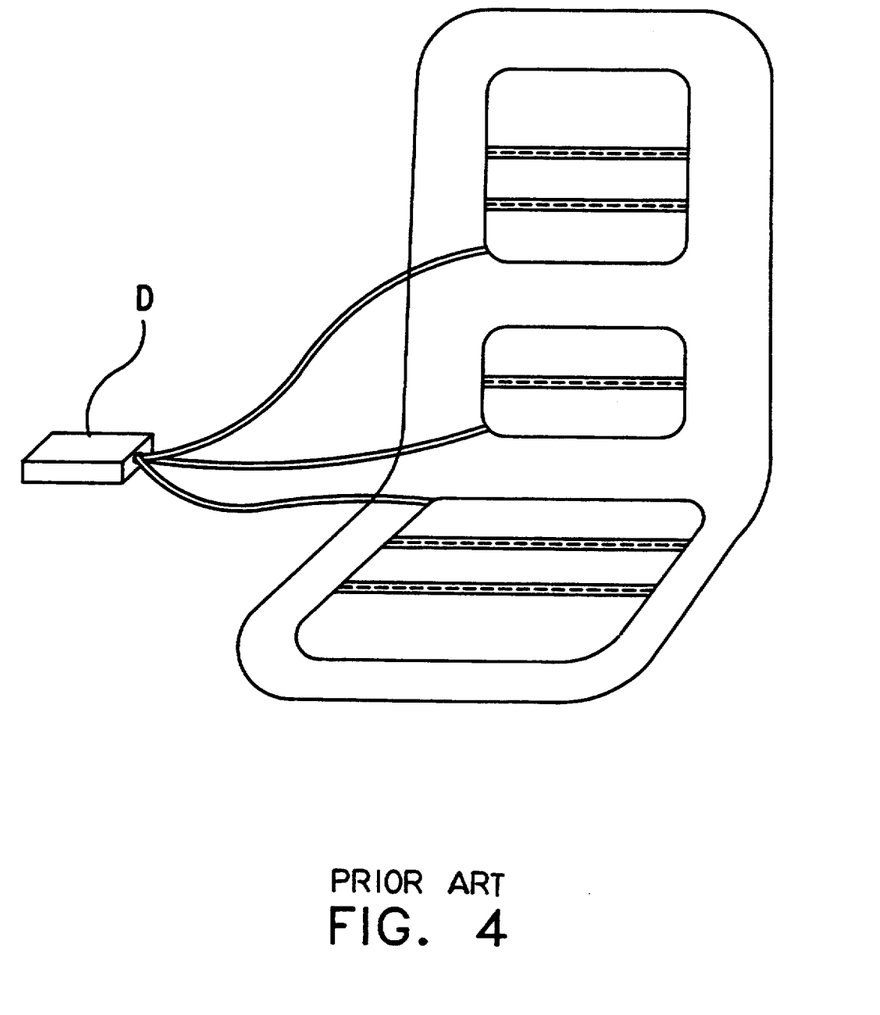
FIG. 4 is a perspective view of the third prior art cushion.

In an effort to enhance the level of comfort for the seat occupant, it is possible for the seat to be designed in such a way as to provide what might be called a heating effect or a vibration effect. That consideration may be particularly important for example in relation to a vehicle seat in which the seat occupant's comfort can be a matter of paramount importance. A commonly used cushion for a seat is shown in FIG. 1, which is simply a soft pad for reclining the user's lumbar region and does not have any other functions. FIG. 2 illustrates another prior art cushion for a seat, which does not have any functions relating to lumbar support, massage or magnetic stimulation, but does provide for a heating effect. Furthermore, such a cushion has no safety means for the heating device so that accidents may happen once the user forgets to turn off the power switch after use. FIGS. 3 and 4 show a third commonly used cushion, which utilizes an external control box D to control an adjustable air pouch A to adapt to the user's lumbar region, a heating device B to produce a heating effect, and a vibration device C to provide a massaging effect. Nevertheless, such a cushion still has the following drawbacks:

1. All functions are controlled by the external control box which is complicated in operation and the cushion may lose all functions once the external control box does not work properly.

2. As an external control box is required for the control of the cushion, the manufacturing cost will be increased significantly making it difficult to be widely used.

3. Since all functions of the cushion are controlled by the external control box, the circuit and structure of the cushion will be complicated and therefore will be more prone to failure.

4. Due to the fact that the cushion is controlled by an external control box, it is necessary to arrange a space to accommodate the external control box thus making it inconvenient to use.

5. The vibration device is mounted on the upper half of the back portion of the cushion, so only the user's back can be massaged.

6. Once the user forgets to turn off the power switch after use, the vibration motor and the heating device may become overheated and burn out thereby wasting energy and potentially causing accidents.

7. As the air pouch is fitted in the lower portion of the back rest of the cushion, the heating device only can be mounted in the upper portion of the back rest of the cushion and cannot be used to provide the right heating effect for the lumbar portion of the user.

8. Such a cushion cannot be used with alternating current, so it is only suited to be used with vehicle seats and cannot be used with any other seats.

9. Such a cushion is so large in size that it is inconvenient for the user to carry or otherwise transport it.

Therefore, it is an object of the present invention to provide a multi-function cushion which can obviate and mitigate the above-mentioned drawbacks.

SUMMARY OF THE INVENTION

This invention relates to an improved multi-function cushion.

It is the primary object of the present invention to provide a multi-function cushion which seldom needs repair and extends durability for longer product life.

It is another object of the present invention to provide a multi-function cushion which has highly reliable safety.

It is still another object of the present invention to provide a multi-function cushion which is of easy operation.

It is still another object of the present invention to provide a multi-function cushion which saves energy.

It is still another object of the present invention to provide a multi-function cushion which is compact in size.

It is still another object of the present invention to provide a multi-function cushion which is low in manufacturing cost.

It is still another object of the present invention to provide a multi-function cushion which can be connected with AC or DC power supply as required.

It is a further object of the present invention to provide a multi-function cushion which is convenient for maintenance and installation.

The other objects and merits and a more full understanding of the present invention will be obtained by those having ordinary skill in the art when the following detailed description of the preferred embodiment is read in conjunction with the accompanying drawings.

DETAILED DESCRIPTION OF THE PREFERRED EMBODIMENT

For the purpose of promoting an understanding of the principles of the invention, reference and specific language will now be made to the embodiment illustrated in the drawings. It will, nevertheless, be understood that no limitation of the scope of the invention is thereby intended; such alternatives and further modifications in the illustrated device, and such further applications of the principles of the invention as illustrated herein would be contemplated as those normally occurring to the one who is skilled in the art to which the invention relates.

Figure 5:
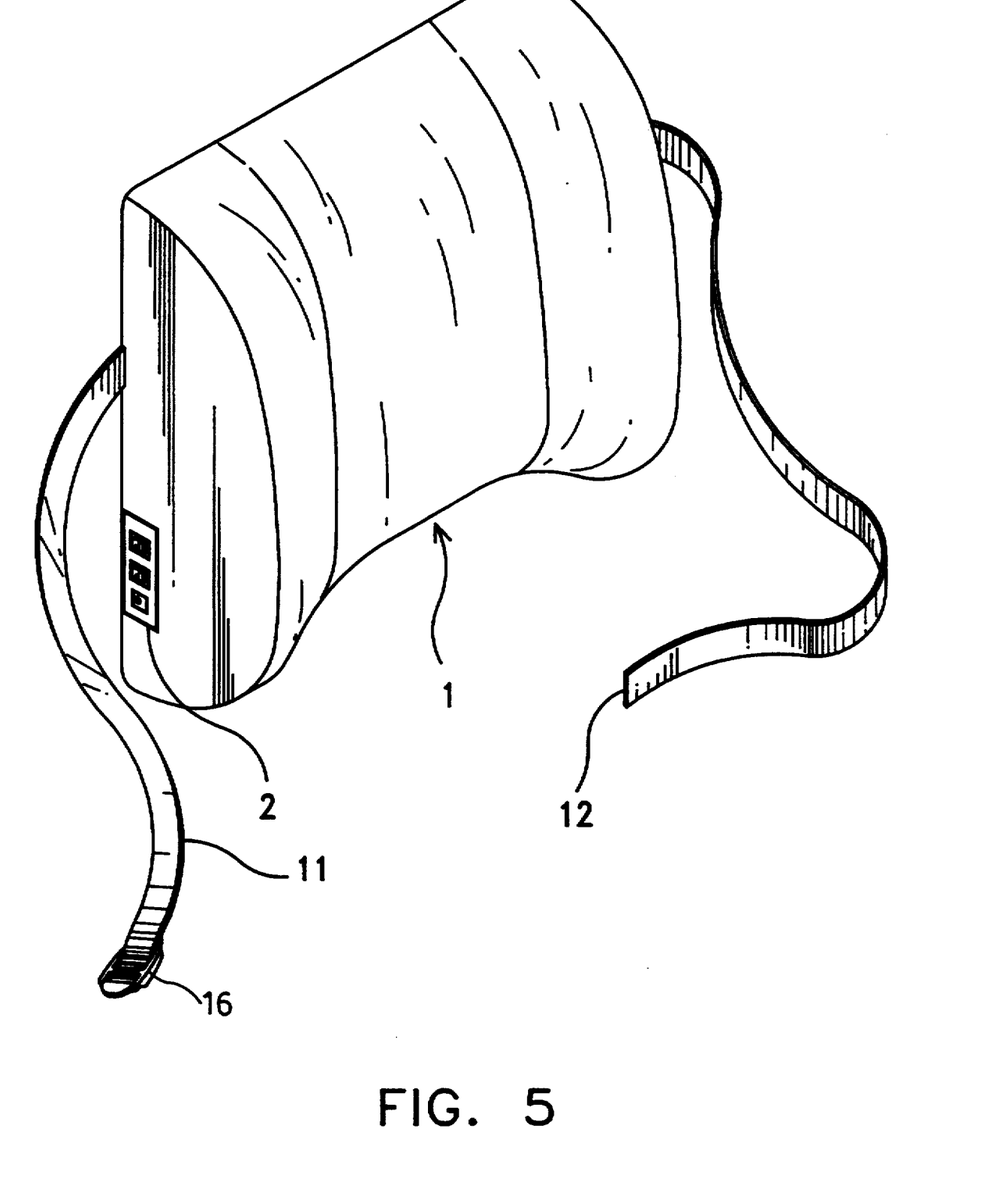
FIG. 5 is a perspective view of the present invention.
Figure 6:
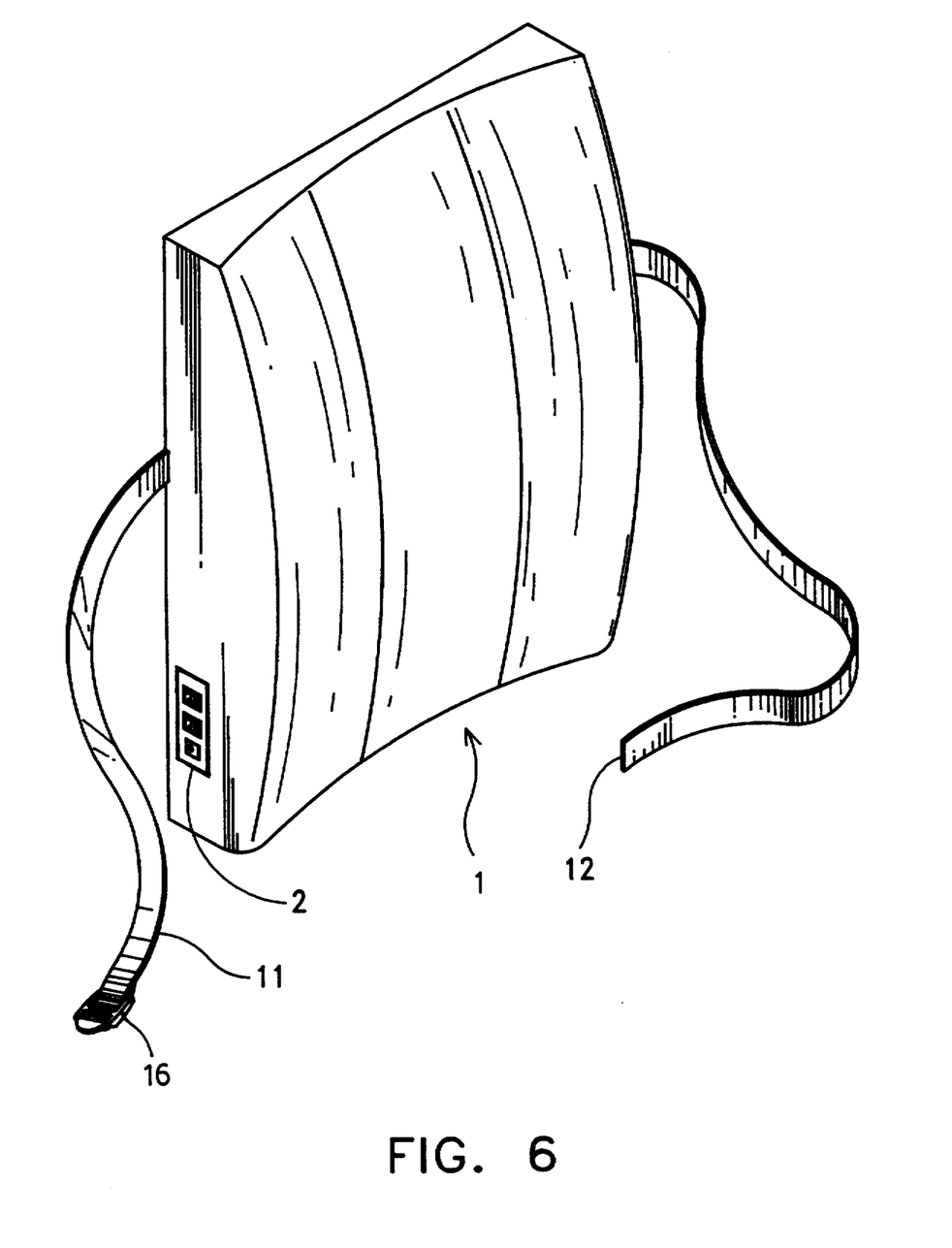
FIG. 6 is a perspective view of a second preferred embodiment according to the present invention.
Figure 7:
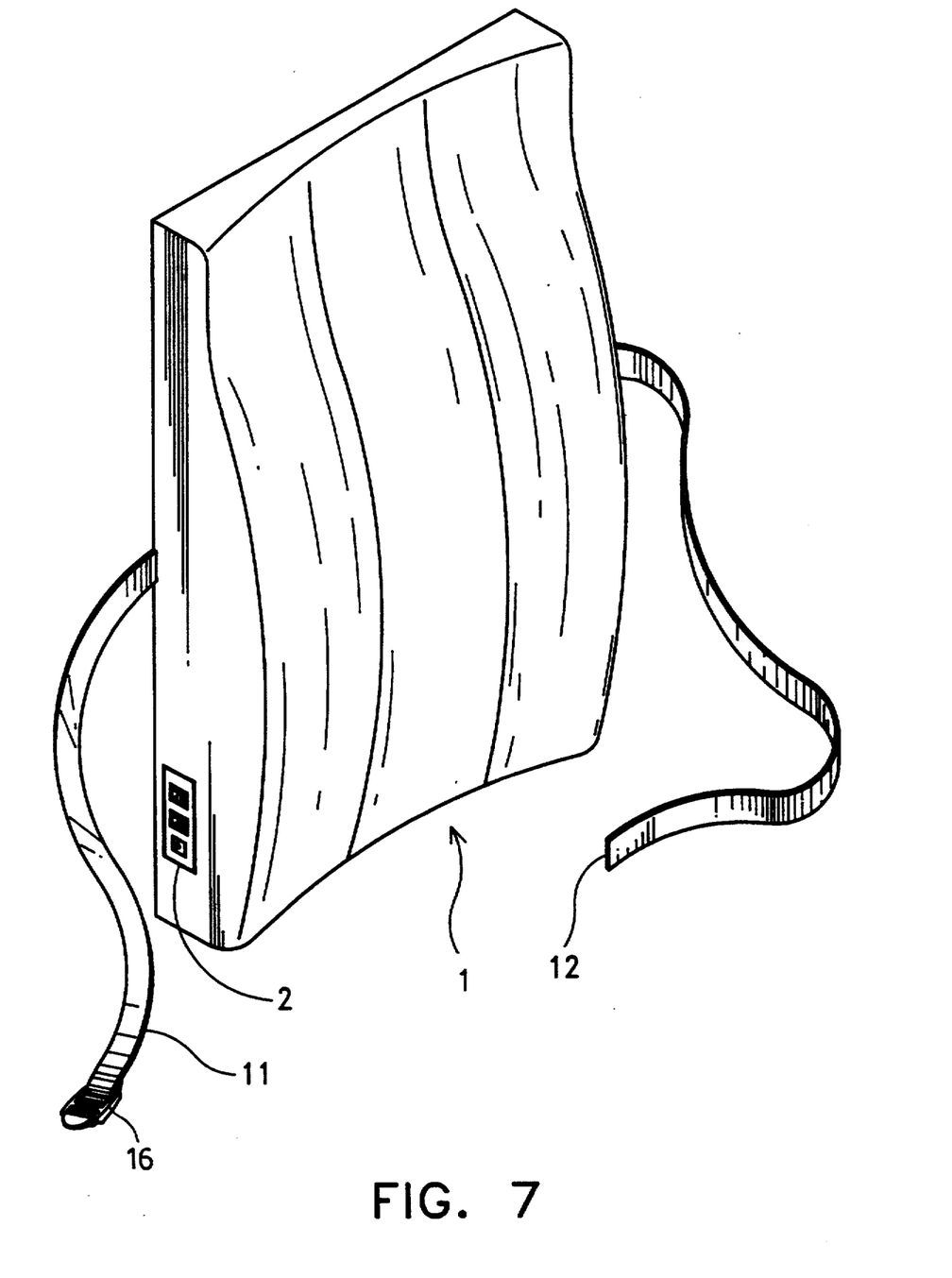
FIG. 7 is a perspective view of a third preferred embodiment according to the present invention.

With reference to the drawings and in particular to FIG. 5 thereof, the multi-function cushion according to the present invention mainly comprises a slip cover 1, two straps 11 and 12, a fitting buckle 16, and a control panel 2.

Figure 8:
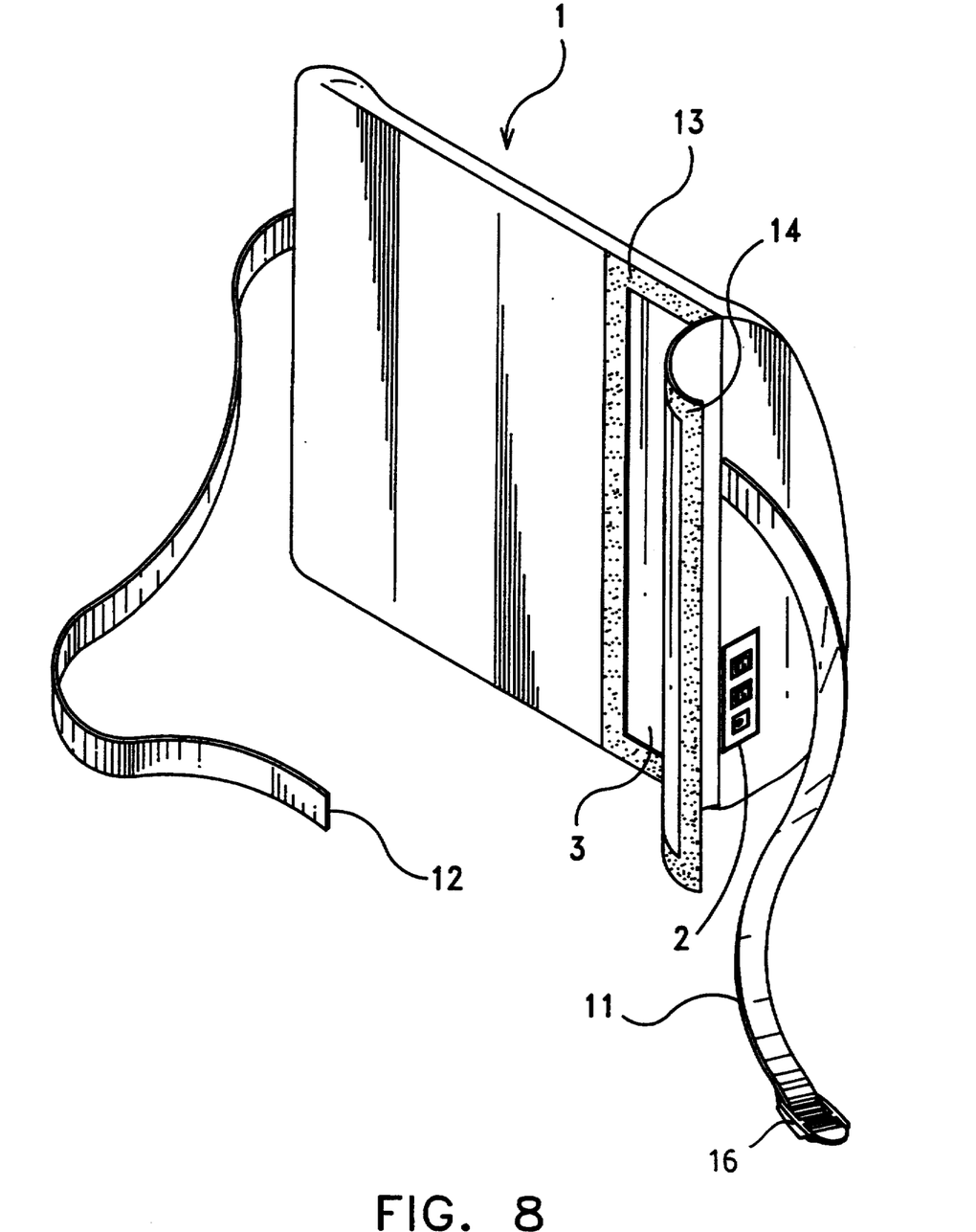
FIG. 8 shows the back side of the present invention.

As illustrated in FIG. 8, the back side of the slip cover 1 is provided with two Velcro strips 13 and 14. Within the slip cover 1 there is a soft pad 3.

Figure 9:
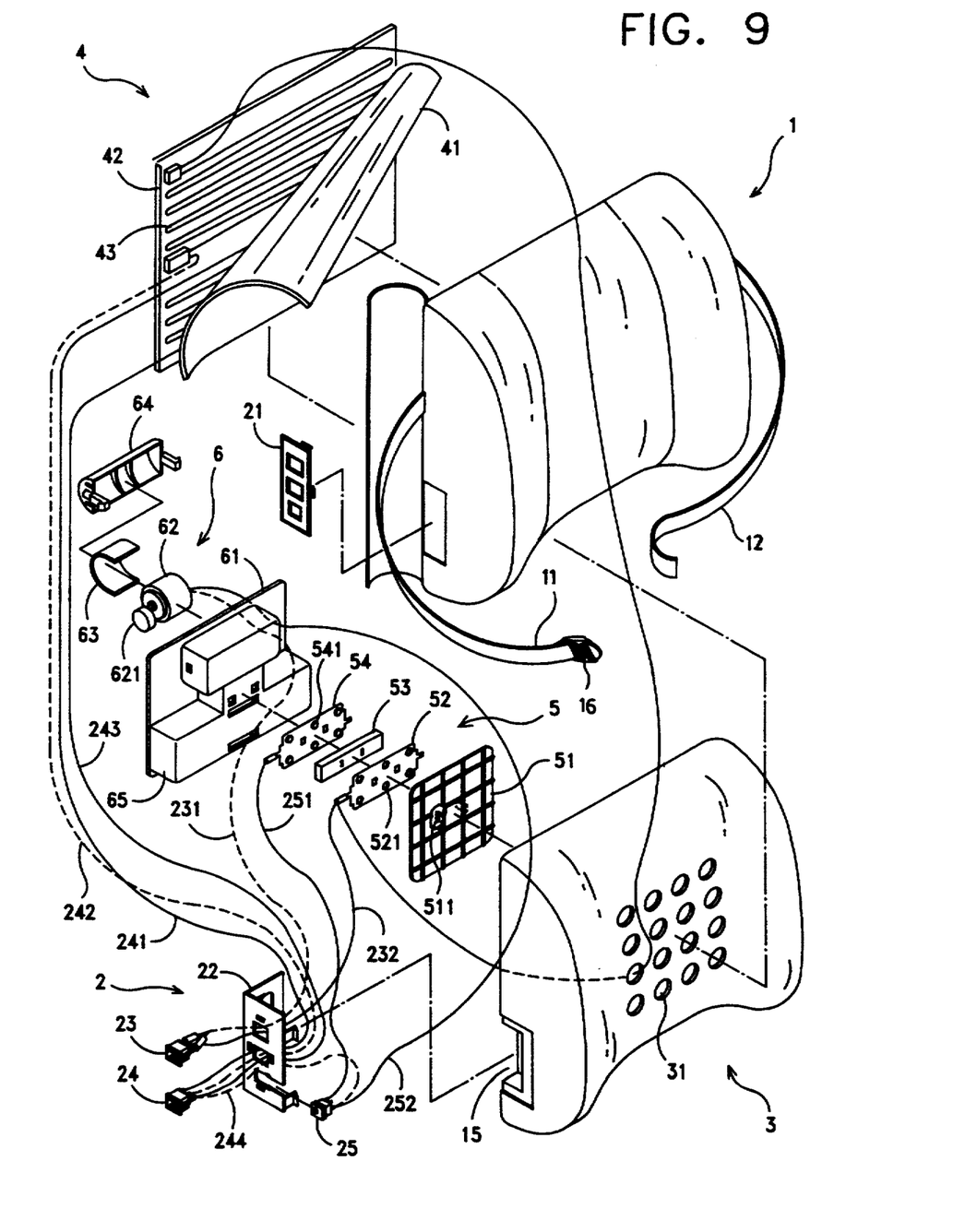
FIG. 9 is an exploded view of the present invention.

Referring to FIG. 9, the control panel 2 is composed of an outer instruction cover 21 and an inner housing chamber 22. The inner housing chamber 22 is fitted in a rectangular opening 15 of the soft pad 3 and can be coupled with the outer instruction cover 21 between the slip cover 1 by a snap fit of cover 21 to housing 22. In the inner housing chamber 22 are mounted a vibration switch 23, a heating switch 24, and a power socket 25. The outer side of the soft pad 3 is provided with a plurality of magnets 31. A heating device 4 electrically connected with the control panel 2 is disposed between the slip cover 1 and the front side of the soft pad 3, and the heating device 4 includes two insulating plates 41 and 42, and a heating circuit 43. Further, there is provided pressure switch 5 and a vibration device 6 in the rear side of the soft pad 3. The pressure switch 5 is electrically connected with the vibration device 6 and the vibration switch 23. The pressure switch 5 includes a press plate 51, a front spring leaf 52, a compressible member 53, and a rear spring leaf 54. The rear side of the press plate 51 has a hook 511. The front spring leaf 52 is formed with a plurality of protuberances 521 on the rear side thereof, while the rear spring leaf 54 has a plurality of protuberances 541 on its front side. The compressible member 53 is made of a resilient material. The hook 511 of the press plate 51 extends through the front spring leaf 52, the compressible member 53 and the rear spring leaf 54 to engage with a housing 61 of the vibration device 6. In addition, a vibration motor 62 is installed within the housing 61 and has a protector 63 on its outer surface. Moreover, the protector 63 is provided with a cover 64 for keeping the vibration motor 62 and the protector 63 together in the housing 61 (see FIG. 10). The lower portion of the housing 61 has a battery chamber 65 for accommodating batteries. Further, the vibration switch 23 is connected with the vibration motor 62 and the front spring leaf 52 via two electrical wires 231 and 232 with different resistance, so that the vibration strength of the vibration motor 62 can be conveniently controlled by the vibration switch 23. The vibration motor 62 will be turned on when the pressure switch 5 is pressed, but it will be turned off when the pressure switch 5 is released. The heating switch 24 is connected to the heating circuit 43 and the power socket 25 through the electrical cords 241, 242, 243 and 244 so that the output power of the heating device 4 will be controlled by the heating switch 24 with different portions of the heating circuit 43 being selectively energized. Furthermore, the heating device 4 will be turned on when the pressure switch 5 is pressed, and it will be turned off when the pressure switch 5 is released. The power socket 25 is connected to the rear spring leaf 54 and the vibration motor 62 via the electrical cords 251 and 252 for connection with an external power supply.

Figure 10:
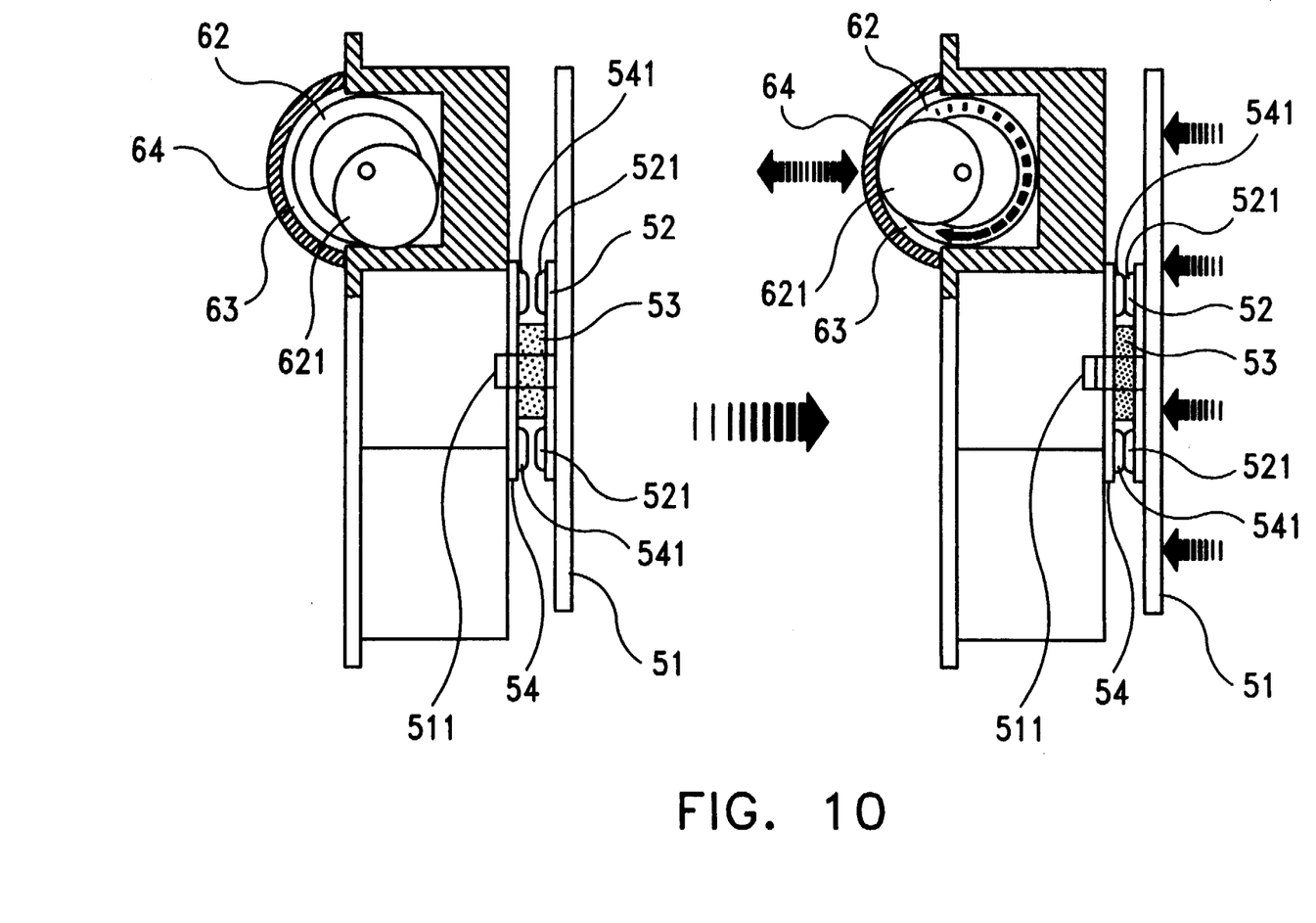
FIG. 10 shows the working principles of the pressure switch of the present invention.

As shown in FIGS. 9 and 10, batteries can be disposed within the battery chamber 65 and when the pressure switch 5 is pressed by the user, the compressible member 53 is compressed and the front spring leaf 52 is forced against the rear spring leaf 54 so that the protuberances 521 of the front spring leaf 52 are in contact with the protuberances 541 of the rear spring leaf 54, thereby turning on the power. Hence, the vibration motor 62 is switched on and cam 621 will be rotated to hit the cover 64 thus producing massaging effect. Further, the heating device on the soft pad 3 will generate heat which will be transmitted to the surface of the slip cover 1. The magnets 31 are used to provide magnetic stimulation to the user. As the pressure switch 5 is released, the power will be turned off and the vibration and heating effects will be suspended. In view of the above, the instant invention has the following advantages:

1. Reliable safety: As the power switch is controlled by a pressure switch, it will be automatically turned off when the cushion is not in use thereby preventing accidents and ensuring safety.

2. Durable product life: The present invention is simple in construction, so it is seldom broken down and the power switch will be automatically turned off when the cushion is not in use thus extending the product life of the cushion.

3. Easy operation: The control panel of the present invention is mounted at one side of the body portion of the cushion and no external controller is required, hence making it easier to operate.

4. Energy-saving: The power switch will be automatically turned off when the cushion is not in use, thereby saving energy.

5. Compact size: As no external controller is required, the present invention is compact in size.

6. Low manufacturing cost: The present invention is simple in structure and does not require an external controller thereby lowering the manufacturing cost thereof.

7. Convenient power sources: The present invention can be adapted to operate from alternating current or direct current, thereby making it convenient in use.

8. Easier maintenance: The slip cover is closed by VELCRO strips thereby enabling it to be easily opened for maintenance.

Although the present invention has been described with a certain degree of particularity, it is understood that the present disclosure is made by way of examples only and that numerous changes in the details of construction and the combination and arrangement of parts can be made without departing from the scope of the application in the invention as hereinafter claimed.

I claim:

1. A multi-function cushion having a portable power source contained therein, comprising:
- a soft pad having opposing front and rear sides and a recess formed in one end of said soft pad, said soft pad having a plurality of magnets disposed on said front side;
- a slip cover releasably secured around said soft pad, said slip cover having a rectangular through opening formed in one end of said slip cover;
- means for generating vibration disposed between said rear side of said soft pad and a first interior surface of said slip cover, said vibration generating means including a housing, and a vibration motor secured to a first side of said housing;
- said portable power source being disposed within said housing;
- means for generating heat disposed between said front side of said soft pad and a second interior surface of said slip cover;
- a control panel housing disposed within said recess of said soft pad and accessible through said rectangular opening formed in said slip cover, said control panel housing including a first control switch electrically coupled to said vibration motor and the portable power source for selective energization of said vibration motor, a second control switch electrically coupled to said heat generating means and the portable power source for selective energization of said heat generating means, and a power socket electrically coupled to said vibration generating means and said heat generating means for electrical coupling of said vibration generating means and said heat generating means with an external power source; and, a pressure switch secured to a second side of said housing of said vibration generating means, said pressure switch being electrically coupled to said vibration motor and said heat generating means for de-energization of said vibration motor and said heat generating means responsive to an absence of pressure applied to said pressure switch.

* * * * *